(12) United States Patent
Maxwell et al.

(10) Patent No.: US 9,867,999 B2
(45) Date of Patent: Jan. 16, 2018

(54) PULSE AMPLIFIER FOR DRIVING ULTRASOUND TRANSDUCERS

(71) Applicants: University of Washington, Seattle, WA (US); The Regents of the University of Michigan, Ann Arbor, MI (US)

(72) Inventors: Adam D. Maxwell, Seattle, WA (US); Bryan Cunitz, Seattle, WA (US); Michael R. Bailey, Seattle, WA (US); Vera Khokhlova, Seattle, WA (US); Timothy L. Hall, Ann Arbor, MI (US)

(73) Assignees: The Regents of the University of Michigan, Ann Arbor, MI (US); University of Washington, Seattle, WA (US)

( * ) Notice: Subject to any disclaimer, the term of this patent is extended or adjusted under 35 U.S.C. 154(b) by 0 days.

(21) Appl. No.: 15/309,394

(22) PCT Filed: May 15, 2015

(86) PCT No.: PCT/US2015/031189
§ 371 (c)(1),
(2) Date: Nov. 7, 2016

(87) PCT Pub. No.: WO2015/176001
PCT Pub. Date: Nov. 19, 2015

(65) Prior Publication Data
US 2017/0072225 A1    Mar. 16, 2017

Related U.S. Application Data

(60) Provisional application No. 61/993,604, filed on May 15, 2014.

(51) Int. Cl.
*A61N 7/00* (2006.01)
*A61B 17/22* (2006.01)
(Continued)

(52) U.S. Cl.
CPC .......... *A61N 7/00* (2013.01); *A61B 17/22004* (2013.01); *A61N 7/02* (2013.01);
(Continued)

(58) Field of Classification Search
CPC ..... B06B 1/0215; B06B 2201/55; A61N 7/00; A61N 2007/0095; A61N 7/02;
(Continued)

(56) References Cited

U.S. PATENT DOCUMENTS 2,963,680 A  * 12/1960  Beebe .................. B06B 1/0215
                                                          367/137
6,047,601 A     4/2000  Foster
(Continued)

FOREIGN PATENT DOCUMENTS

JP        2011-072588 A       4/2011
WO    WO 2015176001 A8  *  7/2016  ........... B06B 1/0215

OTHER PUBLICATIONS

Uemura, S., and C.A. Cain, "Acoustical Evaluation of a Prototype Sector—Vortex Phased-Array Applicator," IEEE Transactions on Ultrasonics, Ferroelectrics, and Frequency Control 39(1)32-38, Jan. 1992.
(Continued)

*Primary Examiner* — Daniel Pihulic
(74) *Attorney, Agent, or Firm* — Christensen O'Connor Johnson Kindness PLLC (57) ABSTRACT

Embodiments of the invention include improved radiofrequency (RF) pulse amplifier systems that incorporate an energy array comprising multiple capacitors connected in parallel. The energy array extends the maximum length of pulses and the maximum achievable peak power output of the amplifier when compared to similar systems. Embodiments also include systems comprising the amplifier configured to drive a load, wherein the load may include one or
(Continued)

more ultrasound (e.g., piezoelectric) transducers Related methods of using the amplifier are also provided.

24 Claims, 6 Drawing Sheets (51) Int. Cl.
  *B06B 1/02* (2006.01)
  *A61N 7/02* (2006.01)
  *G01S 7/52* (2006.01)

(52) U.S. Cl.
  CPC .......... *B06B 1/0215* (2013.01); *G01S 7/5202* (2013.01); *A61N 2007/0073* (2013.01); *A61N 2007/0078* (2013.01); *A61N 2007/0095* (2013.01); *B06B 2201/55* (2013.01)

(58) Field of Classification Search
  CPC .... A61N 2007/0073; A61N 2007/0078; A61B 17/22004; G01S 7/5202
  See application file for complete search history.

(56) References Cited

U.S. PATENT DOCUMENTS

| | | |
|---|---|---|
| 2008/0114255 A1 | 5/2008 | Schwartz et al. |
| 2011/0077517 A1 | 3/2011 | Satou |
| 2014/0073995 A1 | 3/2014 | Teofilovic et al. |
| 2017/0072225 A1* | 3/2017 | Maxwell ............... B06B 1/0215 |

OTHER PUBLICATIONS

International Search Report and Written Opinion dated Aug. 21, 2015, issued in corresponding International Application No. PCT/US15/31189, filed May 15, 2015, 11 pages.

* cited by examiner

PULSE AMPLIFIER FOR DRIVING ULTRASOUND TRANSDUCERS

CROSS-REFERENCE TO RELATED APPLICATION

This application claims benefit of U.S. Provisional Application No. 61/993,604, filed May 15, 2014, the disclosure of which is incorporated by reference herein in its entirety.

STATEMENT OF GOVERNMENT LICENSE RIGHTS

This invention was made with Government support under Grant Nos. 2R01EB007643-05 and 2T32DK007779-11A1, awarded by the National Institutes of Health. The Government has certain rights in the invention.

BACKGROUND

High-intensity focused ultrasound (HIFU) transducers are used to apply ultrasound energy to tissue in a manner that generates localized effects such as heating, boiling, or cavitation of tissue leading to ablation. Presently, HIFU power supplies are available that provide a broad range of driving characteristics. However, high-power (e.g., several kW), long (e.g., millisecond) pulse lengths are achievable only by large, expensive systems that are not feasible for typical clinical use. Emerging techniques, such as boiling histotripsy, require high-power delivery to the ultrasound transducer with long pulse lengths, outside the specifications of commercially available amplifiers. Thus, practical implementation of these techniques would benefit from an improved amplifier that provides these characteristics while retaining a small footprint and relatively low cost.

SUMMARY

In one aspect, an amplification apparatus for generating pulses to drive an ultrasound transducer array is provided. In one embodiment, the apparatus includes:

an amplifier;

an energy array coupled to the amplifier and to a charge power source, the energy array including:

a first energy module having a first capacitance and a first resonant frequency; and a second energy module having a second capacitance and a second resonant frequency, wherein the first energy module and the second energy module are connected in parallel with one another, wherein the first capacitance is greater than the second capacitance, and wherein the second resonant frequency is 2 to 20 times the first resonant frequency, and wherein the energy array is configured to:

store energy from the charge power source to start a pulse generation cycle in response to a first control signal from a control device; and transfer stored energy to generate a pulse for driving the ultrasound transducer array at a driving frequency in response to a second control signal from the control device, wherein the generated pulse has a pulse voltage level of at least 1 Vpp and has a pulse duration time that is in a range of pulse duration times from 0.001 ms to an upper pulse duration time.

In another aspect, a method of generating pulses for driving an ultrasound transducer array is provided. Generally, the disclosed methods utilize an amplifier modified with an energy array as disclosed herein. The amplification provides high power and long pulse lengths.

In one embodiment, the method includes:

providing an energy array that includes a first energy module having a first capacitance and a second energy module having a second capacitance, wherein the first energy module and the second energy module are coupled in parallel with one another;

storing energy in the energy array from a charge power source in response to a first control signal from a control circuit; and transferring energy from the energy array to an amplifier to generate a pulse for driving the ultrasound transducer array in response to a second control signal from the control circuit, wherein the generated pulse has a pulse voltage level of at least 1 Vpp and a pulse duration time within a range of pulse duration times from at least 0.001 ms to an upper pulse duration time.

In another aspect, an ultrasound system is provided. Generally, the disclosed ultrasound system includes an amplifier modified with an energy array as disclosed herein, with the addition of a transducer array (e.g., transducer 112). The transducer array can include any ultrasound transducers capable of being driven by the amplifier.

In one embodiment, the ultrasound system includes:

an amplifier;

an transducer array coupled to the amplifier through a matching network;

an energy array coupled to the amplifier and to a charge power source, the energy array including:

a first energy module having a first capacitance and a first resonant frequency; and a second energy module having a second capacitance and a second resonant frequency, wherein the first energy module and the second energy module are coupled in parallel with one another, wherein the first capacitance is greater than the second capacitance, and wherein the second resonant frequency is 2 to 20 times the first resonant frequency, wherein the amplifier is configured to:

store energy in the energy array from the charge power source to start a pulse generation cycle in response to a first control signal from a control device; and drive the ultrasound transducer array by generating a pulse using energy stored in the energy array in response to a second control signal from the control device, wherein the generated pulse has a pulse voltage level of at least 1 Vpp and a pulse duration time within a range of pulse duration times from at least 0.001 ms to an upper pulse duration time, and wherein the energy array is configured such that the pulse voltage level of the generated pulse varies no more than 10% over the generated pulse.

In another aspect, a method of performing transcutaneous tissue ablation treatment using a transducer array is provided. Generally, the disclosed methods utilize an amplifier modified with an energy array as disclosed herein and coupled to an ultrasound transducer array. Tissue ablation is performed using known methods, but is facilitated by the high power and long pulse lengths of the disclosed amplifier.

In one embodiment, the method includes:

providing an energy array that includes a first energy module having a first capacitance and a second energy module having a second capacitance, wherein the first energy module and the second energy module are coupled in parallel with one another;

storing energy in the energy array from a charge power source in response to a first control signal from a control circuit; and transferring stored energy from the energy array to an amplifier to generate a pulse for driving the transducer array in response to a second control signal from the control circuit, wherein the generated pulse has a pulse voltage level of at least 1 Vpp and a pulse duration time within a range of pulse duration times from at least 0.001 ms to an upper pulse duration time.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Embodiments of the invention include improved radiofrequency (RF) pulse amplifier systems that incorporate an energy array (also referred to herein as a "capacitor array") comprising multiple capacitors connected in parallel. The energy array extends the maximum length of pulses and the maximum achievable peak power output of the amplifier when compared to similar systems. Embodiments also include systems comprising the amplifier configured to drive a load, wherein the load may include one or more ultrasound (e.g., piezoelectric) transducers. Related methods of using the amplifier are also provided.

The disclosed amplifier is relevant to many ultrasound applications. In particular, it may be used for performing both boiling histotripsy and cavitation-based histotripsy. Additionally, it may be used to drive transducers for fragmenting kidney stones with pulsed ultrasound. Furthermore, it may be the driver for ultrasound transducers for shearing chromatin. The disclosed amplifier is an enabling technology in all of these applications which cannot be easily accomplished with a standard radiofrequency amplifier. Continuous wave (CW) amplifiers, although capable of outputting kW power levels, are much too large and expensive to use in a normal laboratory or clinical environment. A more effective approach, as disclosed herein, is to use a pulsed amplifier, capable of output high peak power levels for limited pulse duration. In this regime, the amplifier stores the energy needed for a pulse and delivers it to the load device within the pulse duration, while not requiring a large supply to continuously provide the power from a mains source.

Commercial RF amplifiers output less than 20 kW in the frequency range and bandwidth of the disclosed embodiments. Accordingly, the disclosed amplifier system enables higher power output than commercial RF amplifiers at the desired frequency and bandwidth for ultrasound transducers. Accordingly, in one embodiment the amplifier is configured, using only mains power, to output greater than 20 kW power at a frequency of 10 kHz to 10 MHz with an effective impedance less than 0.1Ω.

Briefly, the energy array attached to the amplifier stores electrical energy that is discharged through the transducer over the duration of a pulse. A low-current DC power supply that can be powered from a normal mains outlet charges the array between pulses. In one embodiment, the energy array is capable of being powered by a residential mains outlet. In a further embodiment, the mains outlet is a U.S. mains outlet (120 V, 60 Hz).

Design of the energy array and its integration with the amplifier requires careful consideration of the components and layout. The total capacitance of the array is determined by the necessary power and pulse duration needed for the amplifier. However, the array includes multiple different sizes of capacitors. These are included because large capacitors are unable to instantaneously provide power due to self-inductance. Smaller capacitors are able to provide current more rapidly, but cannot store large amounts of energy. Thus, multiple capacitor sizes in parallel are used to supply energy to the amplifier over different time periods between, for example, ~50 ns to 10 ms. Tuned damping resistors are included in series with each capacitor to prevent resonances from the self-inductance and capacitance between different capacitors. When modeled and designed correctly, the array acts as an energy storage reservoir with an effective impedance less than 0.1Ω between 100 Hz to greater than 10 MHz frequency.

A secondary result of a proper design is to suppress transient electrical interference in the amplifier system. When the amplifier produces large peak power output, switching of the transistors can cause current transients that lead to corruption of the input signals. At high enough power, this will cause catastrophic failure and damage to the circuit boards. Thus, the capacitor array allows the amplifier to operate at greater peak powers without failure.

Specific aspects and embodiment of the amplifier system will now be described, with reference to the FIGURES, where like numbers indicate like parts.

In one aspect, an amplification apparatus for generating pulses to drive an ultrasound transducer array is provided. In one embodiment, the apparatus includes:

an amplifier;

an energy array coupled to the amplifier and to a charge power source, the energy array including:

a first energy module having a first capacitance and a first resonant frequency; and a second energy module having a second capacitance and a second resonant frequency, wherein the first energy module and the second energy module are connected in parallel with one another, wherein the first capacitance is greater than the second capacitance, and wherein the second resonant frequency is 2 to 20 times the first resonant frequency, and wherein the energy array is configured to:

store energy from the charge power source to start a pulse generation cycle in response to a first control signal from a control device; and transfer stored energy to generate a pulse for driving the ultrasound transducer array at a driving frequency in response to a second control signal from the control device, wherein the generated pulse has a pulse voltage level of at least 1 Vpp and has a pulse duration time that is in a range of pulse duration times from 0.001 ms to an upper pulse duration time.

The amplification apparatus will now be described with reference to FIG. 1, which illustrates the amplification apparatus and related system diagrammatically. The apparatus 100 includes an amplifier 104 at its core that is modified by an energy array 108 in order to more optimally drive an ultrasound transducer 112 in pulsed mode at a high power and long pulse duration.

The amplifier 104 is powered initially by a drive power source 106, which is low voltage (e.g., less than 24 V). In one embodiment, the amplifier 104 is a class D or class E switching voltage amplifier, a device commonly used in audio and radiofrequency power applications.

The shape of the amplified signal is provided by a control device 102. In one embodiment, the control device 102 is a programmable logic device. In one embodiment, the control device is a field-programmable gate-array (FPGA). In other embodiments, the control device is a programmable logic device, such as a programmable logic array (PLA), or a microcontroller. The control device 102 is programmed to output digital signals in a form that provide the input to the amplifier 104 to control the ultrasound center frequency, pulse duration, and pulse repetition frequency. In one embodiment, the control device 102 outputs square-wave signals. In one embodiment, the control device 102 comprises a non-programmable digital logic circuit configured to prevent a short circuit from the energy array to ground.

By combining the functions of the drive power source 106 and the control device 102, the amplifier will output a low power, long pulse duration signal to the transducer 112. However, in order to properly drive the transducer 112 for HIFU operation, higher power amplification is required.

The energy array 108 provides the required power to amplify the pulsed signal from the control device 102, with low impedance, in order to properly power the transducer 112. The energy array 108 comprises capacitors, connected in parallel, which discharge with each pulse. After discharge, the capacitors of the energy array 108 are recharged by a charge power source 110, a high-voltage, low-current DC power supply.

The energy array 108 comprises multiple different sizes and quantities of capacitors designed specifically to work over a large frequency range. When configured correctly, in one embodiment, the array 108 acts as an energy storage reservoir with an effective impedance less than $0.1\Omega$ between 100 Hz to greater than 10 MHz frequency. Unlike most radiofrequency amplifiers, the output impedance of certain embodiments of the disclosed apparatus is very low, which enables its use with almost any ultrasound transducer element.

Finally, the transducer 112 is driven by the amplifier 104, as controlled by the control device 102 and powered by the energy array 108 to produce high-voltage, long duration power pulses. In this regard, the amplifier 104 outputs a high-voltage duplicate of the input signal from the control device 102.

In one embodiment, the energy array 108 is configured to have an impedance less than $0.1\Omega$ over an operating range of frequencies bounded by a lower operating frequency, defined by pulse duration, and an upper operating frequency, defined by the driving frequency of the ultrasound transducer array. The impedance level is dictated by the amplifier 104 output impedance and transducer 112 impedance. The energy array 108 has an output impedance much less—at least 10 times less—than the attached amplifier 104 or transducer 112. The impedance level condition applies to the range of pulse durations and range of operating frequencies disclosed herein.

The system 100 operates with an operating frequency defined by the control device 102. This operating frequency relates to the transducer 112. In one embodiment, the operating frequency range is from 10 kHz to 10 MHz.

The system 100 operates with a pulse duration time defined by the control device 102. The pulse duration time is from a lower pulse duration time of 0.001 ms to an upper pulse duration time. In one embodiment, the upper pulse duration time is greater than or equal to 10 ms and less than or equal to 1 second. In a further embodiment, related to the upper pulse duration time, the lower pulse frequency is less than or equal to 100 Hz.

The system 100 produces peak power at a particular pulse frequency and pulse duration. In one embodiment, the peak power is at least 1 kW. In one embodiment, the peak power is at least 10 kW. In one embodiment, the peak power is at least 30 kW. In one embodiment, the peak powers previous disclosed are at a frequency of at least 1 MHz. In one embodiment, the peak powers previous disclosed are at a frequency of at least 1 ms. In one embodiment, the peak power is less than 100 kW.

Figure 1:
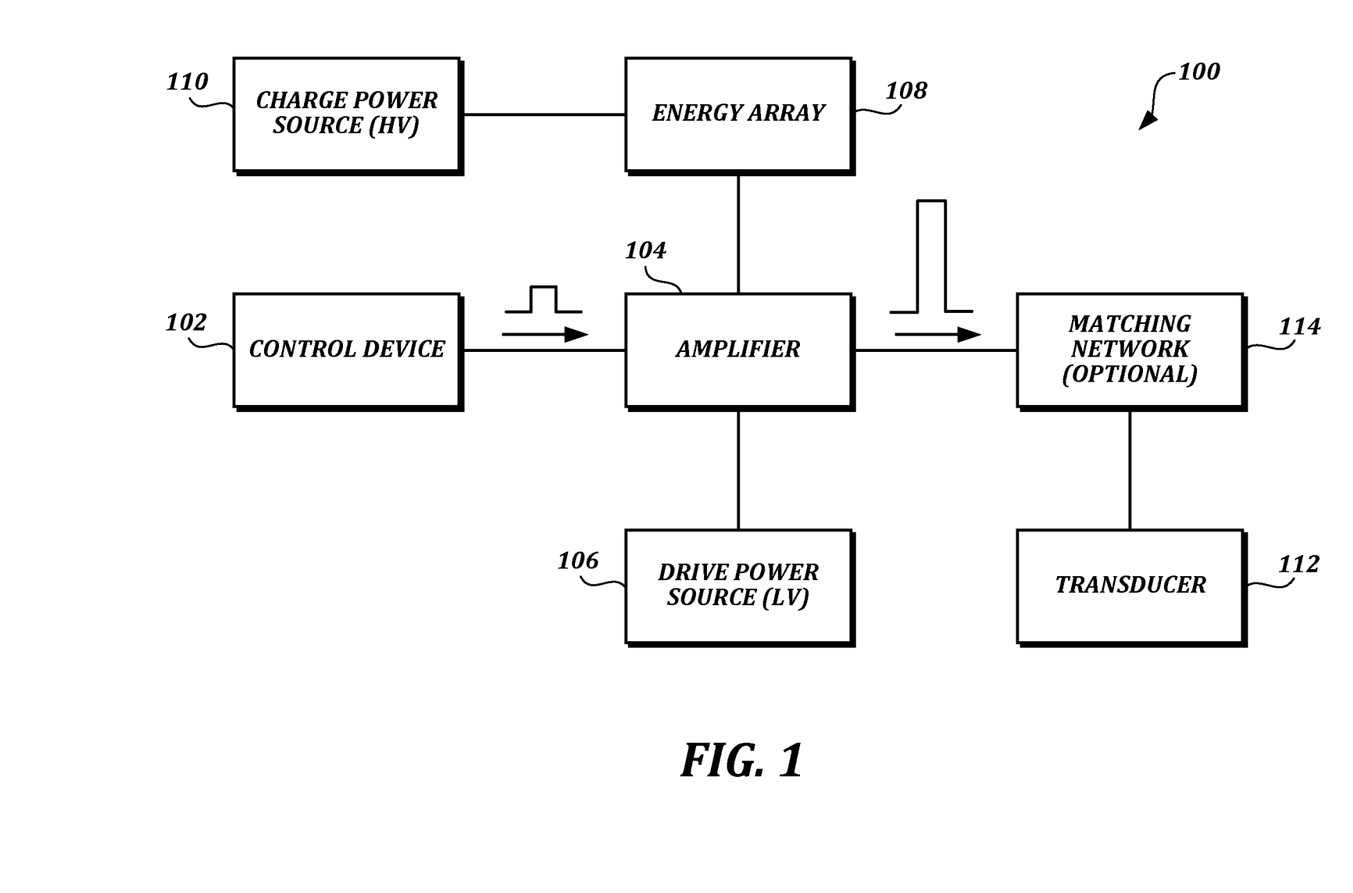
FIG. 1 diagrammatically illustrates an amplification system in accordance with the disclosed embodiments.

As illustrated in FIG. 1, an optional matching network 114 can be used to filter the amplifier 104 output, a square signal, to create sinusoidal voltage bursts that drive the transducer 112 elements. Such a matching network 114, coupled with the low impedance of the array 108 and system 100 allows for essentially any type of transducer 112 (or transducer array) to be driven efficiently. Accordingly, in one embodiment, the amplifier is coupled to an impedance matching network and the amplifier is connectable to the ultrasound transducer array through the impedance matching network. In one embodiment, the matching network is an L-type matching network. In a further embodiment, the matching network is a transformer-based matching network.

Figure 2A:
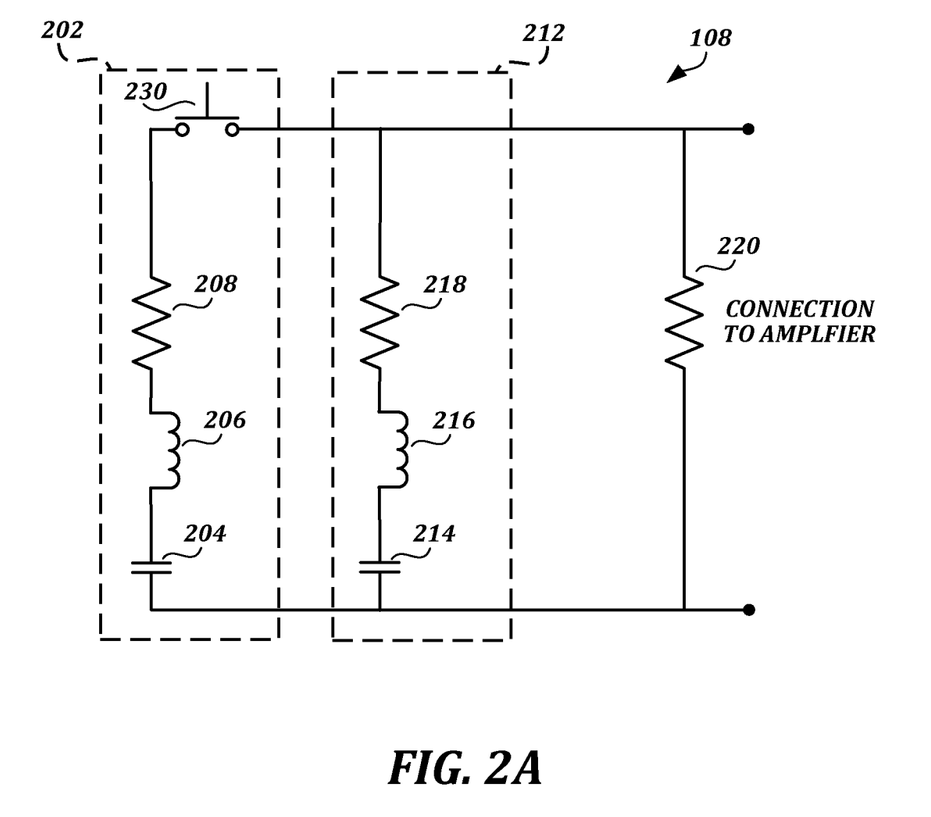
FIGS. 2A-2C are circuit diagrams of energy arrays in accordance with the disclosed embodiments.

Referring to FIG. 2A, a diagram of an embodiment of the energy array 108 is illustrated. In the illustrated embodiment, a first energy module 202 and a second energy module 212 are included. Each energy module 202, 212 includes a capacitor: a first capacitor 204 having a first capacitance; and a second capacitor 214 having a second capacitance that is different from the first capacitance. Each energy module 202, 212 have an intrinsic inductance 206, 216 and resistance 208, 218.

A relay 230 can disconnect a large-value capacitors 204 from the amplifier 104 to prevent immediate discharge during shutdown.

The capacitors 204 and 214 have different capacitance values, with the capacitance of the first energy module 202 being greater than that of the second energy module 212. The need for different capacitances is because large capacitors are unable to instantaneously provide power due to self-inductance. Smaller capacitors are able to provide current more rapidly, but cannot store large amounts of energy. Therefore, multiple capacitor sizes in parallel are used to supply energy to the amplifier over different time periods. In one embodiment, the first energy module 202 is a high-capacitance module and has a capacitance of 1 to 50 mF. In a further embodiment, the second energy module 212 is a low-capacitance module with a capacitance of between a factor of 2 and 20 less than the capacitance of the first energy module 202.

Each energy module in the array 108 has a resonant frequency. Therefore, the first energy module 202 has a first resonant frequency and the second energy module 212 has a second resonant frequency. All capacitors have a resonant frequency, above which they behave inductively. In the array 108, the capacitors 204, 214 are configured to have resonant frequencies "spaced" apart in order to reduce the impact of these resonance frequencies during operation of the array 108 comprising many capacitors. Accordingly, the capacitors 204, 214 are selected such that the resonant frequencies are spaced apart by a multiple of between 2 and 20. In a further embodiment, the capacitors of the array 108 are selected such that the resonant frequencies are space apart by a multiple of between 5 and 15. Capacitor resonant frequency design considerations are discussed in further detail below.

Finally, the energy array 108 includes a shunt resistor 220 adjacent the connection to the amplifier 108.

During operation, the energy array 108 is configured to store energy from the charge power source 110 to start a pulse generation cycle in response to a first control signal from the control device 102.

During operation, the energy array 108 is then configured to transfer stored energy to the amplifier 104 to generate a pulse for driving the ultrasound transducer array 112 at a driving frequency in response to a second control signal from the control device 102. The generated pulse has a pulse voltage level of at least 1 Vpp. In another embodiment, the generated pulse has a pulse voltage level of at least 10 Vpp. In another embodiment, the generated pulse has a pulse voltage level of at least 100 Vpp. In another embodiment, the generated pulse has a pulse voltage level of 10 kVpp or less.

In one embodiment, the generated pulse has a pulse duration time that is in a range of pulse duration times from 0.001 ms to an upper pulse duration time. In one embodiment, the upper pulse duration time is 40 ms or less. In one embodiment, the pulse duration time (from lower to upper) 0.0002 ms to 40 ms. In one embodiment, the pulse duration time (from lower to upper) 0.0005 ms to 10 ms. In one embodiment, the pulse duration time (from lower to upper) 0.001 ms to 1 ms.

In one embodiment, the energy array is configured to provide energy from the first energy module after providing energy from the second energy module. Generally, the voltage across the energy modules is equal during a pulse; however, smaller capacitors typically discharge faster than larger capacitors.

In one embodiment, the energy array is configured such that the pulse voltage (e.g., from the power supply) level varies by no more than 10% over the generated pulse. The peak-to-peak voltage generated on the transducer is proportional to power supply voltage. Thus, to ensure the pulse output power is sufficiently constant throughout the pulse, the supply voltage must be maintained.

Figure 2B:
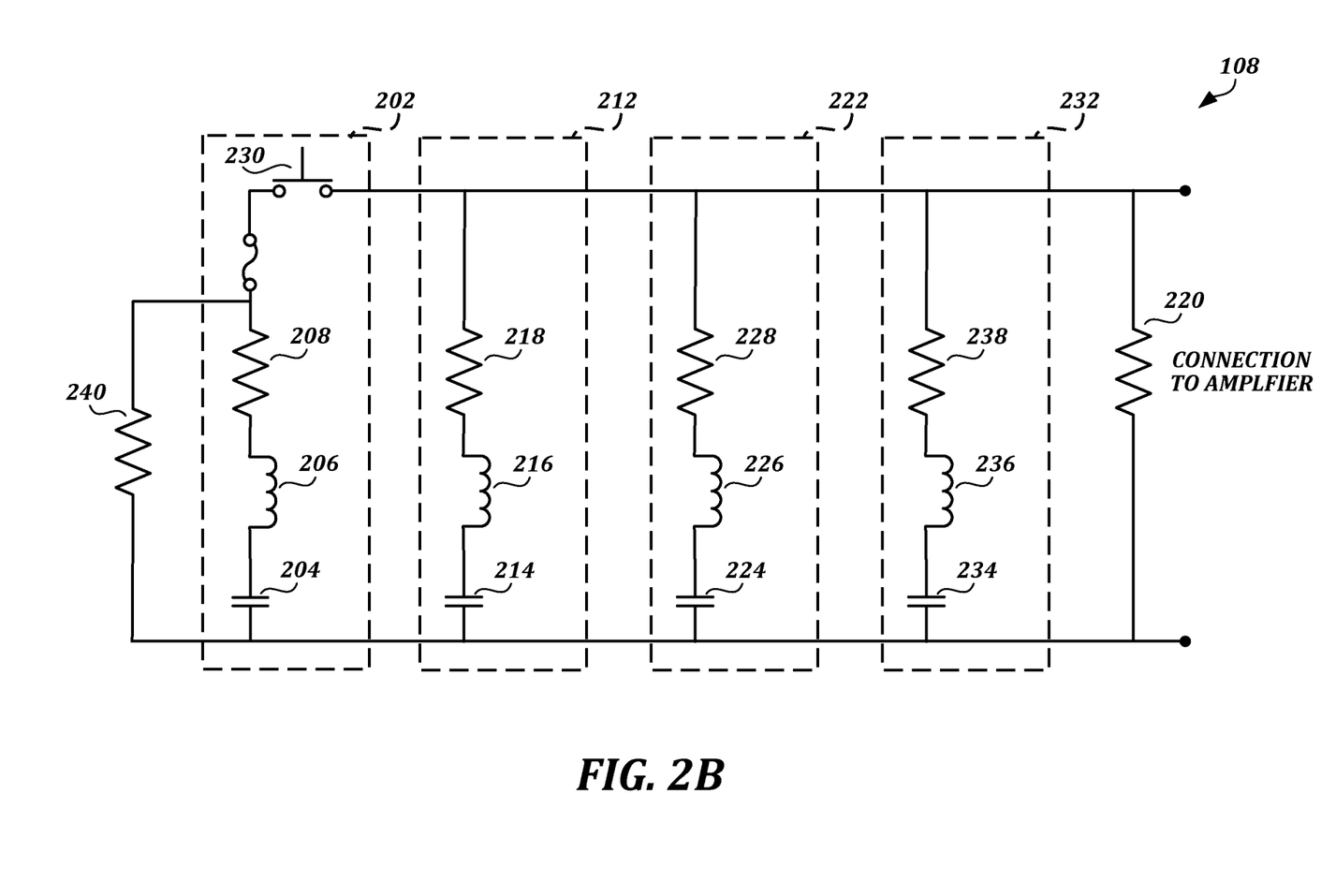

In another embodiment of an energy array 108, illustrated in FIG. 2B, additional features beyond those of FIG. 2A are included. Notably, a third energy module is included, comprising a third capacitor 224, an inductance 226, and a resistance 228. Further, a fourth energy module is included, comprising a fourth capacitor 234, an inductance 236, and a resistance 238. In one embodiment, all four energy modules 202, 212, 222, and 232 have different capacitances. In another embodiment, there are a plurality of at least one of the types of energy modules 202, 212, 222, and 232, connected in parallel. For example, in one embodiment there are two or more forth energy modules 232 in the energy array 108.

Still referring to FIG. 2B, a resistor 240 is included as a safety measure to "bleed off" stored charge in the energy array 108 after operation of the amplifier 104 concludes. The resistor 240 has a resistance of 0.1-1 MΩ in one embodiment. As a further safety measure, a fuse 231 is included.

Figure 2C:
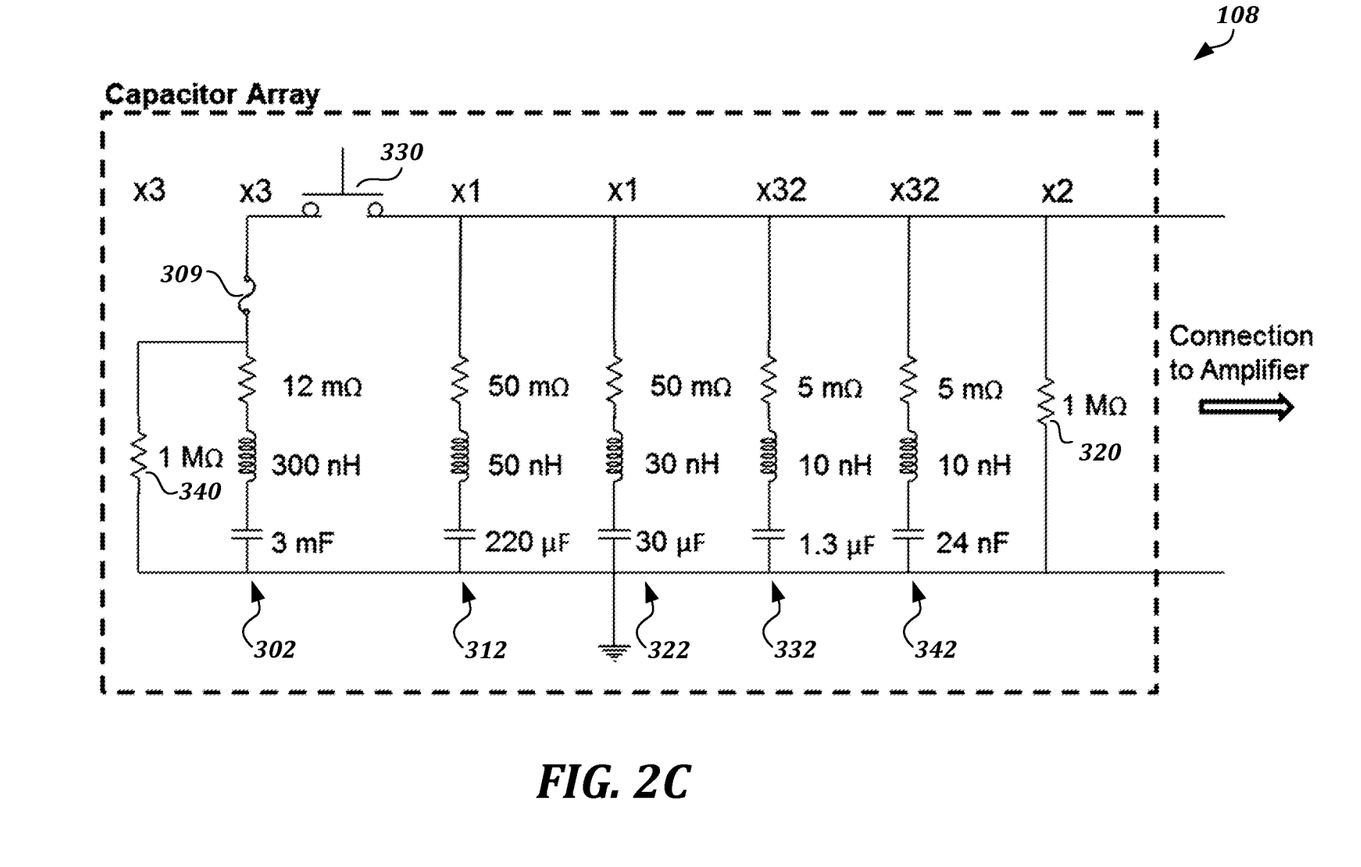

FIG. 2C is an electrical schematic of an equivalent layout for one embodiment of a capacitor energy array. In the illustrated embodiment, each branch of the array includes a capacitor with intrinsic inductance and resistance. The energy array 108 includes five energy modules 302, 312, 322, 332, and 342, each having different capacitances. The number of energy modules of each type is shown at the top of the module as ×#. For example, there are 32 of the energy modules 332. With regard to terminology, each grouping of one or more capacitors having the same capacitance is referred to as an energy module. If there are multiple capacitors within an energy module, each of those is individually referred to as a "submodule." Therefore, in FIG. 2C, there are 32 submodules within energy module 332. There are no submodules in energy module 312 because there is only a single capacitor, based on the "×1" designation above the energy module 312. Submodules are connected in parallel with each other and within the greater energy array 108. The use of submodules allows for fine tuning of the capacitance of each energy module to achieve the desired characteristics of the energy array 108.

The array 108 also includes damping 340 and shunt 320 resistors, and a fuse 309 for the large-value (3 mF) energy modules 302. A relay 330 disconnects the large-value capacitors from the amplifier to prevent immediate discharge during shutdown.

The fuse 309, in one embodiment, is a fast-blow fuse, coupled in series with at least one capacitor of the array 108. In a further embodiment, the fast-blow fuse amperage is determined by the upper pulse duration and maximum power.

As illustrated by FIGS. 2B and 2C, the energy array 108 can be configured to include any number of capacitor types (i.e., capacitance values) and any number of each type of each capacitor type, as needed to achieve the desired performance. The number of energy modules can be tailored, depending on the desired range of frequencies and pulse durations needed in the array. Because the resonant frequencies of the capacitors are spaced by approximately 10×, then one energy module is needed per decade of the frequency range. For example, the specific case of a frequency range of 100 Hz to 10 MHz covers 5 decades and so five capacitor types are used.

The energy array 108 illustrated in FIG. 2C is a specific exemplary embodiment with five energy that is further described in Example 1, below.

Accordingly, in one embodiment, the energy array further includes:
a third energy module having a third capacitance;
a fourth energy module having a fourth capacitance; and
a fifth energy module having a fifth capacitance,
wherein the first, second, third, fourth, and fifth energy modules are coupled in parallel with one another, and
wherein the third capacitance is less than both the first capacitance and the second capacitance.

In a further embodiment, the fifth energy module includes a plurality of energy submodules each having capacitance,
wherein the energy submodules of the fifth energy module are coupled in parallel with one another, and
wherein the quantity of energy submodules of the fifth energy module is such that the impedance of the energy array is less than 0.1Ω for the range of pulse duration times.

In a further embodiment, the fourth energy module includes a plurality of energy submodules, each having a capacitance, wherein the energy submodules of the fourth energy module are coupled in parallel with one another, wherein the quantity of energy submodules of the fourth energy module is such that the impedance of the energy array is less than 0.1Ω for the range of pulse duration times, and wherein the capacitances of the energy submodules of the fifth energy modules are less than the capacitances of the energy submodules of the fourth energy module.

In a further embodiment, the third energy modules has a third resonance frequency, wherein the third energy module is configured such that the third resonance frequency is between 2 and 20 times the second resonance frequency.

In a further embodiment, the fourth and fifth energy modules have a fourth and a fifth resonance frequency, respectively, wherein the fourth energy module is configured such that the fourth resonance frequency is between 2 and 20 times the third resonance frequency, and wherein the fifth energy module is configured such that the fifth resonance frequency is between 2 and 20 times the fourth resonance frequency.

In one embodiment, the first energy module includes at least one first capacitor, wherein the second energy module includes at least one second capacitor that has a lower capacitance than the first capacitor, wherein the third energy module includes at least one third capacitor that has a lower capacitance than the second capacitor, wherein the fourth energy module includes at least one fourth capacitor that has a lower capacitance than the third capacitor, and wherein the fifth energy module includes at least one fifth capacitor that lower capacitance than the fourth capacitor.

In one embodiment, the first energy module includes at least two first capacitors coupled in parallel with one another, wherein the fourth energy module includes at least 30 fourth capacitors coupled in parallel with one another, and wherein the fifth energy module includes at least 30 fifth capacitors coupled in parallel with one another.

In one embodiment, the first capacitor has a capacitance of about 3 mF, the second capacitor has a capacitance of about 220 µF, the third capacitor has a capacitance of about 30 µF, the fourth capacitor has a capacitance of about 1.2 µF, and the fifth capacitor has a capacitance of about 24 nF. As used herein, the term "about" indicates that the subject number can be modified by plus or minus 10% and still fall within the described embodiment.

In one embodiment, at least one of the third, fourth, or fifth energy modules further includes a resistor coupled in series with at least one of the third, fourth, or fifth capacitors to dampen the impedance of the energy array.

In one embodiment, the fifth capacitance is less than 900 nF, and wherein the fifth energy module comprises at least 30 energy submodules coupled in parallel with one another, wherein each energy submodules of the fifth energy module each have a capacitance less than 40 nF.

In one embodiment, the energy array is coupled to one or more solid state or electromechanical relays configured to discharge energy stored in the energy array through a grounding path in response to the charge power source being deactivated.

Design of the Energy Array

The amplifier system uses the energy array combined with a high-voltage power supply to generate and sustain large transient outputs to drive ultrasound transducers. The capacitor array, when configured properly, is able to provide large currents to the amplifier very quickly over a finite pulse duration, without causing fluctuations in the high-voltage line that can lead to undesirable operation of the amplifier. This is accomplished by careful selection of capacitors and addition of series inductance and resistance to each capacitor value in the array.

In an ideal case, the power supply provides a stable DC voltage that does not fluctuate over time. Power supplies cannot response instantly to a change in load, however, so there is usually a delay in its ability to source current. To compensate for this action, bypass capacitors (capacitors placed across the high-voltage terminals) are utilized. These capacitors store energy that can quickly be transferred when the amplifier is active. To determine the capacitor values several steps are followed.

1. Determining the Overall Capacitance of the System

The overall capacitance is first determined according to Equation 1 by the maximum output pulse duration and power needed in for single pulse. In Equation 1, E is the energy stored in joules, C is the overall system capacitance, $V_{DC}$ is the DC voltage across the energy array, $P_{el}$ is the pulse-average power, PD is the pulse duration, and Z is the impedance of the transducer at the driving frequency.

$$E = \frac{1}{2}CV_{DC}^2 = P_{el} \cdot PD \Rightarrow C = \frac{PD}{4Z} \quad \text{(Eq. 1)}$$

For the exemplary system of the Examples below, a specified the pulse duration (PD)=10 ms and the load impedance on each channel $Z_{CH}$=10Ω, with 8 channels total. The combined impedance Z=1.25Ω.

Thus, C=0.002 F can store the energy needed for one pulse. However, a capacitance significantly larger than this is needed to ensure the voltage does not change significantly over this time frame. A 10% decrease in voltage corresponds with a 19% decrease in energy, thus the total capacitance should be C*1/0.19=10.5 mF. For the exemplary array, 9 mF is provided via three 3 mF capacitors.

In one embodiment, the energy array has an overall capacitance greater than the upper pulse duration time divided by an impedance of the ultrasound transducer array.

2. Determining Additional Capacitor Values

Large-value capacitors are used to provide the energy storage in step 1, but additional capacitors are needed within the system. This is because all capacitors have a resonant frequency, above which they behave inductively. Larger capacitors inherently have lower resonant frequency, and as such, only work with low frequency or over a long response time. Starting with the resonant frequency of the power capacitors, additional capacitors are added in parallel that have resonant frequencies spaced by approximately a factor of 10. Depending on how many different values are selected for use, this spacing or factor may vary, such as multiples between 2 and 20. The number of each size capacitor is chosen to ensure the impedance between the terminals will be sufficiently low (less than 0.1Ω) in the frequency range of interest for the capacitor. As an example of the impedance of the amplifier system without impedance "dampening," FIG. 3A shows the impedance of a capacitor array with five capacitor sizes in parallel (3 mF, 220 µF, 30 µF, 1.3 µF, and 0.025 µF).

3. Tuning Frequency Response

Figure 3A:
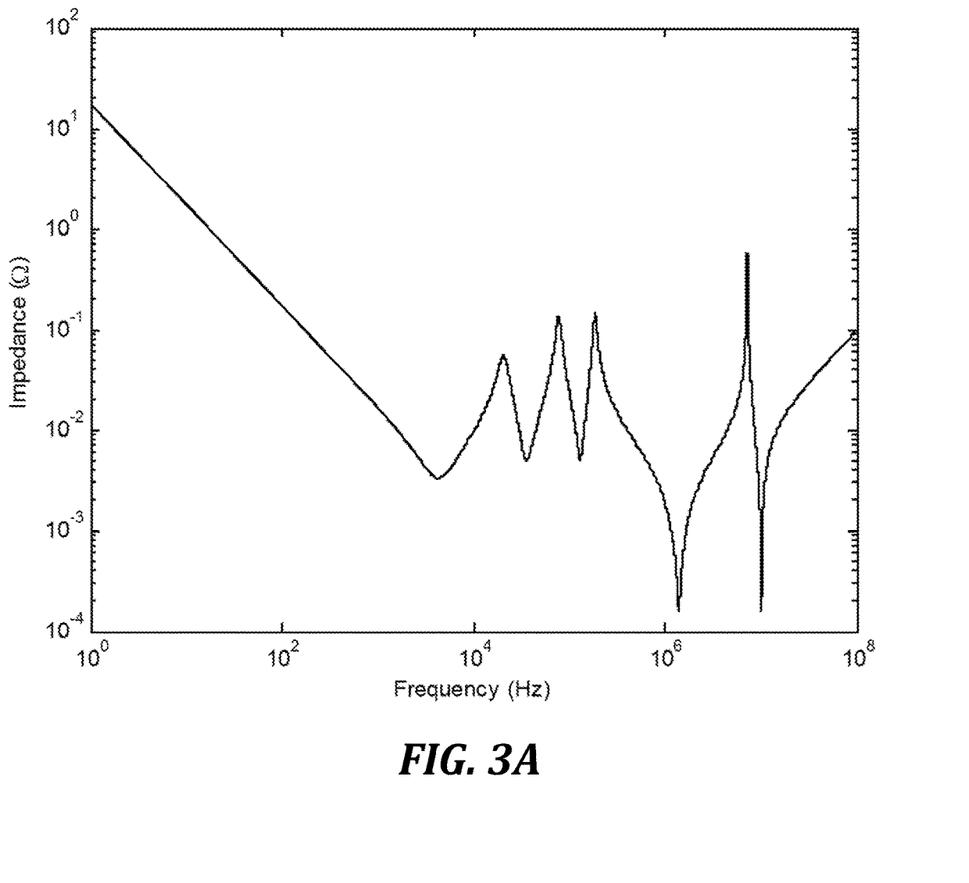
FIG. 3A graphically illustrates the impedance of an exemplary capacitor array with five capacitor sizes in parallel (3 mF, 220 µF, 30 µF, 1.3 µF, and 0.025 µF)
Figure 3B:
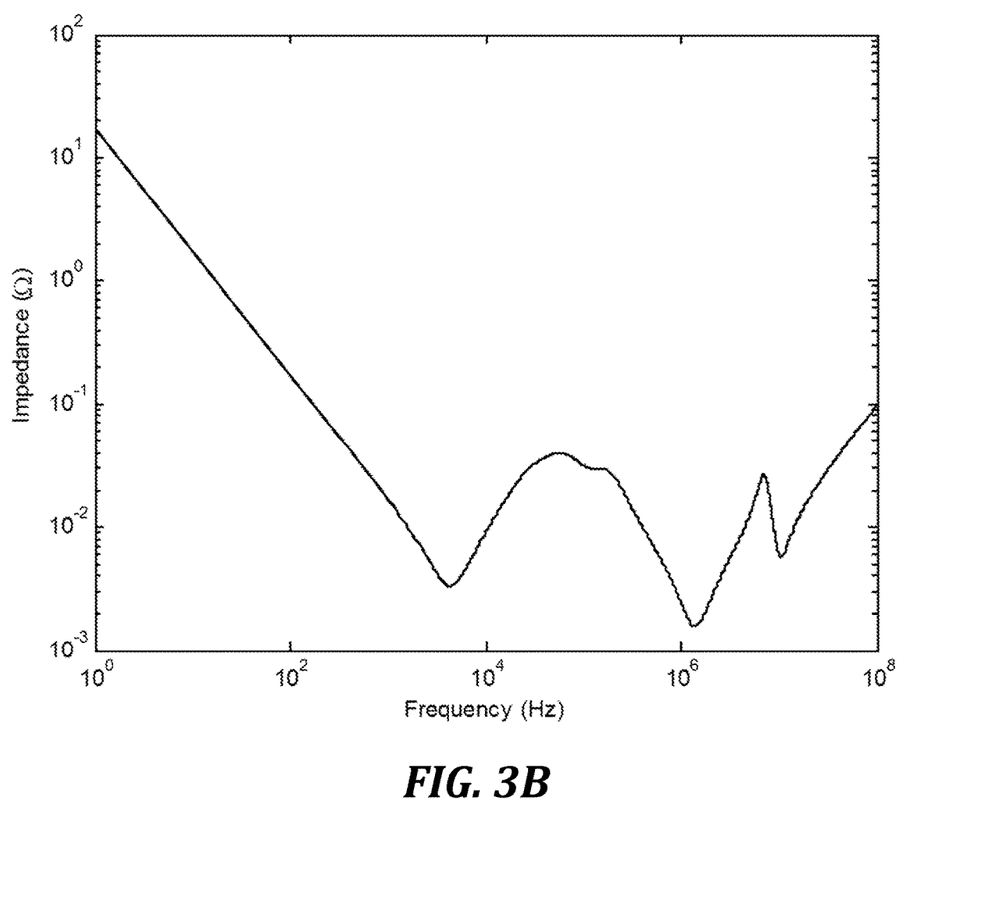
FIG. 3B graphically illustrates the impedance of the capacitor array characterized in FIG. 3A with the addition of resistors in series with the capacitors of each energy module of the array, in order to reduce the impedance at certain frequencies.

Note in FIG. 3A that the impedance is low over the frequency range of interest (greater than 100 Hz), but there are several points of higher impedance due to resonance between different capacitors. This effect can lead to ringing of the supply at these high-impedance points. To minimize the effect, small resistances are added in series to each capacitor to dampen such resonances. As noted in FIG. 2B, each energy module has a resistance (208, 218, 228, 238) that can be inherent, or can also be an added resistor to address resonance issues. In FIG. 2C, each energy module includes a resistor of mΩ magnitude. As a result of adding such resistors, FIG. 3B shows a "dampened" version of the same array characterized in FIG. 3A, with resistance added. Small resistors (e.g., mΩ) are added in series to each capacitor to dampen such resonances. Note that the impedance of the exemplary amplifier system meets the goal of less than 0.1Ω between 100 Hz and 20 MHz.

Amplification Methods

In another aspect, a method of generating pulses for driving an ultrasound transducer array is provided. Generally, the disclosed methods utilize an amplifier modified with an energy array as disclosed herein. The amplification provides high power and long pulse lengths.

In one embodiment, the method includes:

providing an energy array that includes a first energy module having a first capacitance and a second energy module having a second capacitance, wherein the first energy module and the second energy module are coupled in parallel with one another;

storing energy in the energy array from a charge power source in response to a first control signal from a control circuit; and transferring energy from the energy array to an amplifier to generate a pulse for driving the ultrasound transducer array in response to a second control signal from the control circuit, wherein the generated pulse has a pulse voltage level of at least 1 Vpp and a pulse duration time within a range of pulse duration times from at least 0.001 ms to an upper pulse duration time.

In one embodiment, providing the energy array comprises providing an energy array having an overall capacitance greater than the upper pulse duration time divided by the impedance of the ultrasound transducer array.

In one embodiment, transferring stored energy from the energy array to the amplifier comprises transferring stored energy from the first energy module after transferring stored energy from the second energy module.

In one embodiment, providing an energy array further comprises:

providing a third energy module having a third capacitance;

providing a fourth energy module having a fourth capacitance; and providing a fifth energy module having a fifth capacitance, wherein the first, second, third, fourth, and fifth energy modules are coupled in parallel with one another, and wherein the second capacitance is greater than the third capacitance.

In one embodiment, the first energy module includes a plurality of energy submodules each having a first capacitor, wherein the energy submodules of the first energy module are coupled in parallel with one another.

In one embodiment, the third energy module has a third resonance frequency, and wherein the third resonance frequency is between 2 and 20 times the second resonance frequency.

In one embodiment, the fourth and fifth energy modules have a fourth and a fifth resonance frequency, respectively, wherein the fourth resonance frequency is between 2 and 20 times the third resonance frequency, and wherein the fifth resonance frequency is between 2 and 20 times the fourth resonance frequency.

In one embodiment, the high pulse duration time is at least 8 ms.

In one embodiment, the impedance of the energy array is less than 0.1Ω for the pulse duration times within the range of pulse duration times.

In one embodiment, the method further includes providing one or more resistors in series with one or more capacitors of the first, second, third, fourth, or fifth energy modules to dampen the impedance of the energy array.

Ultrasound System

In another aspect, an ultrasound system is provided. Generally, the disclosed ultrasound system includes an amplifier modified with an energy array as disclosed herein, with the addition of a transducer array (e.g., transducer 112). The transducer array can include any ultrasound transducers capable of being driven by the amplifier.

In one embodiment, the ultrasound system includes:

an amplifier;

an transducer array coupled to the amplifier through a matching network;

an energy array coupled to the amplifier and to a charge power source, the energy array including:

a first energy module having a first capacitance and a first resonant frequency; and a second energy module having a second capacitance and a second resonant frequency, wherein the first energy module and the second energy module are coupled in parallel with one another, wherein the first capacitance is greater than the second capacitance, and wherein the second resonant frequency is 2 to 20 times the first resonant frequency, wherein the amplifier is configured to:

store energy in the energy array from the charge power source to start a pulse generation cycle in response to a first control signal from a control device; and drive the ultrasound transducer array by generating a pulse using energy stored in the energy array in response to a second control signal from the control device, wherein the generated pulse has a pulse voltage level of at least 1 Vpp and a pulse duration time within a range of pulse duration times from at least 0.001 ms to an upper pulse duration time, and wherein the energy array is configured such that the pulse voltage level of the generated pulse varies no more than 10% over the generated pulse.

Method of Performing Transcutaneous Tissue Ablation Treatment

In another aspect, a method of performing transcutaneous tissue ablation treatment using a transducer array is provided. Generally, the disclosed methods utilize an amplifier modified with an energy array as disclosed herein and coupled to an ultrasound transducer array. Tissue ablation is performed using known methods, but is facilitated by the high power and long pulse lengths of the disclosed amplifier.

In one embodiment, the method includes:

providing an energy array that includes a first energy module having a first capacitance and a second energy module having a second capacitance, wherein the first energy module and the second energy module are coupled in parallel with one another;

storing energy in the energy array from a charge power source in response to a first control signal from a control circuit; and transferring stored energy from the energy array to an amplifier to generate a pulse for driving the transducer array in response to a second control signal from the control circuit, wherein the generated pulse has a pulse voltage level of at least 1 Vpp and a pulse duration time within a range of pulse duration times from at least 0.001 ms to an upper pulse duration time.

Example 2 discloses generating histotripsy lesions in tissue according to the disclosed embodiments.

The following examples are included for the purpose of illustrating, not limiting, the described embodiments.

EXAMPLES

Example 1: Design of a HIFU Amplification System

Our innovation includes an electronic amplifier system (FIG. 1) for delivering power to piezoelectric ultrasound transducers. The amplifier includes a modified device for driving high intensity focused ultrasound (HIFU) arrays, the primary functional improvement being to extend the maximum length of pulses the amplifier can deliver at high power from ~100 μs to ≥10 ms. The modifications also serve to increase the maximum peak power output beyond the original capabilities. An embodiment of the system has been tested to produce 36 kW peak power, and we calculate it can produce ~90 kW peak power for pulse durations up to 10 ms at 1 MHz.

The amplifier is a class D switching voltage amplifier, a device commonly used in audio and radiofrequency power applications. A field-programmable gate-array (FPGA) board is programmed to output 3.3V digital signals in the form of square-wave bursts that provide the input to the amplifier to control the ultrasound center frequency, pulse duration, and pulse repetition frequency. The amplifier outputs a high-voltage duplicate of the input signal, which is then filtered through an L-type matching network to create sinusoidal voltage bursts that drive the transducer elements. A key feature of this particular system is that, unlike most radiofrequency amplifiers, the output impedance can be very low (~1.5Ω for a single channel of the present system), which enables its use for almost any transducer element.

The amplifier has been modified by addition of a high-voltage capacitor array and features to protect against immediate discharge of the capacitor array for the safety of the operator and amplifier itself.

The capacitor array stores electrical energy that is discharged through the transducer over the duration of a pulse. A low-current DC power supply charges the capacitor array between pulses. FIG. 2C illustrates the exemplary energy array 108 used with a class D amplifier. In embodiments, each branch of the array comprises or consists of a capacitor with intrinsic inductance and resistance, as well as damping and shunt resistors, and fuses for large-value capacitors. A relay disconnects the large-value capacitors from the amplifier to prevent immediate discharge during shutdown. The values (×#) above each series indicate the number of series circuits connected in parallel for each capacitor or shunt value shown in the array.

Design of the capacitor array and its integration with the amplifier is not trivial. The total capacitance of the array is determined by the necessary power and pulse duration needed for the amplifier. However, the array includes of multiple different sizes of capacitors. These are included because large capacitors are unable to instantaneously provide power due to self-inductance. Smaller capacitors are able to provide current more rapidly, but cannot store large amounts of energy. Thus, multiple capacitor sizes in parallel are used to supply energy to the amplifier over different time periods between ~50 ns to 10 ms. Tuned damping resistors are included in series with each capacitor to prevent resonances from the self-inductance and capacitance between different capacitors. When modeled and designed correctly, the array acts as an energy storage reservoir with an effective impedance less than 0.1Ω between 100 Hz to greater than 10 MHz frequency.

A secondary result of a proper design is to suppress transient electrical interference in the amplifier system. When the amplifier requires large peak power output, switching of the transistors can cause current transients that lead to corruption of the input signals. At high enough power, this will cause catastrophic failure and damage to the circuit boards. Thus, the capacitor array allows the amplifier to operate at greater peak powers without failure.

Protective measures for the amplifier include the installation of fast-blow fuses in line with each large-value capacitor, digital logic installed on the amplifier board preventing the possibility of a short from the capacitors to ground, and redundant power supplies to the FPGA board so that it cannot be disabled accidentally. Additionally, solid state relays can be implemented to disconnect the capacitor bank from the amplifier upon shutdown of the DC supply and drain the charge through a safe grounding path. This amplifier is relevant to many ultrasound applications. For example, it may be used for performing both boiling histotripsy and cavitation-based histotripsy. Additionally, it may be used to drive transducers for fragmenting kidney stones with pulsed ultrasound. Finally, it may be the driver for a ultrasound transducer for shearing chromatin. It is an enabling technology in all of these applications that could not be easily accomplished with a standard radiofrequency amplifier.

Example 2: Generating Histotripsy Lesions in Tissue

OBJECTIVES: Mechanical disintegration of soft tissues has been demonstrated with pulsed high-intensity focused ultrasound. This method utilizes shock wave exposures combined with HIFU-induced boiling or cavitation to break down the targeted tissue into homogeneous, liquefied debris with no indication of thermal damage. This work presents a system for generating histotripsy lesions in tissue through significant overlying tissue paths.

METHODS: A 1-MHz piezoelectric focused transducer with 14.7-cm diameter and 14-cm focal length was built as a confocal 7-element assembly. An RF amplifier was constructed to apply up to 30 kW electrical pulse-average power to the transducer for pulse durations up to 10 ms. These parameters provided capability to operate the transducer in both boiling histotripsy and cavitation histotripsy modes. The transducer output was characterized by nonlinear modeling based on the Westervelt equation using measurements from acoustic holography to set a boundary condition. The transducer hologram was measured at low power in a 5.5-cm prefocal plane, and nonlinear simulations were performed at greater power levels. Simulated results were compared with direct measurement of the focal pressure using a fiber-optic hydrophone. Lesions were generated with the system in ex vivo bovine liver at depths up to 6 cm. A derating procedure developed for nonlinear highly-focused HIFU fields was used (with attenuation=0.5 dB/cm/MHz) to scale the output pressure to compensate for energy losses at different depths.

RESULTS: Focal waveforms could be measured with a hydrophone up to 30% maximum pressure output. Above this level, simulations provided acoustic parameters of the field, but cavitation prevented measurement.

Lesions were formed in liver with shock waves above an in situ pressure threshold of p+=77 MPa and p−=14 MPa for 10 ms pulse lengths. Initial measurements indicated that the thresholds for forming histotripsy lesions at different depths could be accurately estimated from derating within ~10% of the amplitude. Experimentally, lesions were achieved at 6 cm depth at 26% of the maximum pressure amplitude of the array, leaving the possibility for deeper treatments.

CONCLUSIONS: The results suggest that current transducer technologies enable delivery of boiling histotripsy therapy at clinically-relevant depths, and a combined measurement and modeling approach can be used for treatment planning.

While illustrative embodiments have been illustrated and described, it will be appreciated that various changes can be made therein without departing from the spirit and scope of the invention.

The invention claimed is:

1. An apparatus for generating pulses to drive an ultrasound transducer array, the apparatus comprising:
    an amplifier;
    an energy array coupled to the amplifier and to a charge power source, the energy array including:
        a first energy module having a first capacitance and a first resonant frequency; and
        a second energy module having a second capacitance and a second resonant frequency,
        wherein the first energy module and the second energy module are connected in parallel with one another, wherein the first capacitance is greater than the second capacitance, and wherein the second resonant frequency is 2 to 20 times the first resonant frequency, and
    wherein the energy array is configured to:
        store energy from the charge power source to start a pulse generation cycle in response to a first control signal from a control device; and
        transfer stored energy to generate a pulse for driving the ultrasound transducer array at a driving frequency in response to a second control signal from the control device, wherein the generated pulse has a pulse voltage level of at least 1 Vpp and has a pulse duration time that is in a range of pulse duration times from 0.001 ms to an upper pulse duration time.

2. The apparatus of claim 1, wherein the energy array has an overall capacitance greater than the upper pulse duration time divided by an impedance of the ultrasound transducer array.

3. The apparatus of claim 2, wherein the energy array further includes:
    a third energy module having a third capacitance;
    a fourth energy module having a fourth capacitance; and
    a fifth energy module having a fifth capacitance,
    wherein the first, second, third, fourth, and fifth energy modules are coupled in parallel with one another, and
    wherein the third capacitance is less than both the first capacitance and the second capacitance.

4. The apparatus of claim 3, wherein the energy array is configured to have an impedance less than 0.1Ω over an operating range of frequencies bounded by a lower operating frequency, defined by pulse duration, and an upper operating frequency, defined by the driving frequency of the ultrasound transducer array.

5. The apparatus of claim 4, wherein the upper pulse duration time is greater than or equal to 10 ms and less than or equal to 1 second, and wherein an upper pulse frequency is greater than or equal to 10 MHz.

6. The apparatus of claim 5,
    wherein the fifth energy module includes a plurality of energy submodules each having capacitance,
    wherein the energy submodules of the fifth energy module are coupled in parallel with one another, and
    wherein the quantity of energy submodules of the fifth energy module is such that the impedance of the energy array is less than 0.1Ω for the range of pulse duration times.

7. The apparatus of claim 6,
    wherein the fourth energy module includes a plurality of energy submodules, each having a capacitance,
    wherein the energy submodules of the fourth energy module are coupled in parallel with one another,
    wherein the quantity of energy submodules of the fourth energy module is such that the impedance of the energy array is less than 0.1Ω for the range of pulse duration times, and
    wherein the capacitances of the energy submodules of the fifth energy modules are less than the capacitances of the energy submodules of the fourth energy module.

8. The apparatus of claim 4,
    wherein the third energy modules has a third resonance frequency,
    wherein the third energy module is configured such that the third resonance frequency is between 2 and 20 times the second resonance frequency.

9. The apparatus of claim 8,
    wherein the fourth and fifth energy modules have a fourth and a fifth resonance frequency, respectively,
    wherein the fourth energy module is configured such that the fourth resonance frequency is between 2 and 20 times the third resonance frequency, and
    wherein the fifth energy module is configured such that the fifth resonance frequency is between 2 and 20 times the fourth resonance frequency.

10. The apparatus of claim 9, wherein the amplifier device is configured to produce at least 36 kW of peak power at a pulse frequency of 1 MHz and a pulse duration time of 10 ms.

11. The apparatus of claim 1, wherein the amplifier comprises a class D switching amplifier or a class E switching amplifier.

12. The apparatus of claim 4,
    wherein the first energy module includes at least one first capacitor,
    wherein the second energy module includes at least one second capacitor that has a lower capacitance than the first capacitor,
    wherein the third energy module includes at least one third capacitor that has a lower capacitance than the second capacitor, wherein the fourth energy module includes at least one fourth capacitor that has a lower capacitance than the third capacitor, and
wherein the fifth energy module includes at least one fifth capacitor that lower capacitance than the fourth capacitor.

13. The apparatus of claim 12, wherein the first energy module includes at least two first capacitors coupled in parallel with one another,
wherein the fourth energy module includes at least 30 fourth capacitors coupled in parallel with one another, and
wherein the fifth energy module includes at least 30 fifth capacitors coupled in parallel with one another.

14. The apparatus of claim 13, wherein the first capacitor has a capacitance of about 3 mF, the second capacitor has a capacitance of about 220 µF, the third capacitor has a capacitance of about 30 µF, the fourth capacitor has a capacitance of about 1.2 µF, and the fifth capacitor has a capacitance of about 24 nF.

15. The apparatus of claim 12, wherein at least one of the third, fourth, or fifth energy modules further includes a resistor coupled in series with at least one of the third, fourth, or fifth capacitors to dampen the impedance of the energy array.

16. The apparatus of claim 12, further comprising a fast-blow fuse coupled in series with the at least one first capacitor.

17. The apparatus of claim 4, wherein the control device comprises a programmable logic device.

18. The apparatus of claim 4, wherein the control device comprises a non-programmable digital logic circuit configured to prevent a short circuit from the energy array to ground.

19. The apparatus of claim 4, wherein the fifth capacitance is less than 900 nF, and wherein the fifth energy module comprises at least 30 energy submodules coupled in parallel with one another, wherein each energy submodules of the fifth energy module each have a capacitance less than 40 nF.

20. The apparatus of claim 1, wherein the energy array is configured to provide energy from the first energy module after providing energy from the second energy module.

21. The apparatus of claim 1, wherein the energy array is configured such that the pulse voltage level varies by no more than 10% over the generated pulse.

22. The apparatus of claim 4, wherein the energy array is coupled to one or more solid state or electromechanical relays configured to discharge energy stored in the energy array through a grounding path in response to the charge power source being deactivated.

23. The apparatus of claim 1, wherein the amplifier is coupled to an impedance matching network and the amplifier is connectable to the ultrasound transducer array through the impedance matching network.

24. An ultrasound system comprising:
an amplifier;
a transducer array coupled to the amplifier through a matching network;
an energy array coupled to the amplifier and to a charge power source, the energy array including:
a first energy module having a first capacitance and a first resonant frequency; and
a second energy module having a second capacitance and a second resonant frequency,
wherein the first energy module and the second energy module are coupled in parallel with one another, wherein the first capacitance is greater than the second capacitance, and wherein the second resonant frequency is 2 to 20 times the first resonant frequency,
wherein the amplifier is configured to:
store energy in the energy array from the charge power source to start a pulse generation cycle in response to a first control signal from a control device; and
drive the ultrasound transducer array by generating a pulse using energy stored in the energy array in response to a second control signal from the control device, wherein the generated pulse has a pulse voltage level of at least 1 Vpp and a pulse duration time within a range of pulse duration times from at least 0.001 ms to an upper pulse duration time, and
wherein the energy array is configured such that the pulse voltage level of the generated pulse varies no more than 10% over the generated pulse.

* * * * *

UNITED STATES PATENT AND TRADEMARK OFFICE
CERTIFICATE OF CORRECTION

PATENT NO.         : 9,867,999 B2
APPLICATION NO.    : 15/309394
DATED              : January 16, 2018
INVENTOR(S)        : A. D. Maxwell et al.

It is certified that error appears in the above-identified patent and that said Letters Patent is hereby corrected as shown below:

Column 17, Line 5 Claim 12:
"that lower" should read --that has a lower--

Signed and Sealed this
Nineteenth Day of June, 2018

Andrei Iancu
*Director of the United States Patent and Trademark Office*